United States Patent [19]

Nagabhushan et al.

[11] Patent Number: 4,740,598
[45] Date of Patent: Apr. 26, 1988

[54] CONVERSION OF ARISTEROMYCIN INTO CYCLARADINE

[75] Inventors: Tattanahali L. Nagabhushan, Parsippany; Doris P. Schumacher, Florham Park, both of N.J.

[73] Assignee: Schering Corporation, Kenilworth, N.J.

[21] Appl. No.: 842,093

[22] Filed: May 20, 1986

[51] Int. Cl.$^4$ .................... C07D 473/32; A61K 31/52
[52] U.S. Cl. ...................................... 544/277; 544/276
[58] Field of Search ................. 544/276, 277; 514/261

[56] References Cited

U.S. PATENT DOCUMENTS 4,138,562  2/1979  Vince et al. .......................... 544/326

OTHER PUBLICATIONS

T. L. Nagabhushan et al., Abstracts of Papers presented at the 185th ACS National Meeting, Seattle, Washington 1983–CARB #27.

T. W. Greene, "Protective Groups in Organic Synthesis", Wiley-Interscience, N.Y., Chapter 2, pp. 10–86.

T. Kusaka et al., The Journal of Antibiotics, vol. XXI, pp. 255–263 (1968).

H. C. Brown et al., J. Am. Chem. Soc., vol. 92 (1970), pp. 709–710.

H. O. House, Modern Synthetic Reactions, 2nd Ed W. A. Benjamin, Inc. N.Y., 1972, pp. 54–70.

E. J. Corey et al., J. Am. Chem. Soc., vol. 93 (1971), pp. 1491–1493 and 7319–7320.

F. Hansske et al., Tetrahedron, vol. 40, No. 1 (1984), pp. 125–135.

*Primary Examiner*—Nicholas S. Rizzo
*Attorney, Agent, or Firm*—Thomas D. Hoffman; Gerald S. Rosen

[57] ABSTRACT

A process for the conversion of aristeromycin into cyclaradine via. The stereoselective reduction of a 3',5'-di-O-protected-2'-keto derivative of aristeromycin is disclosed.

13 Claims, 1 Drawing Sheet

U.S. Patent
Apr. 26, 1988
4,740,598
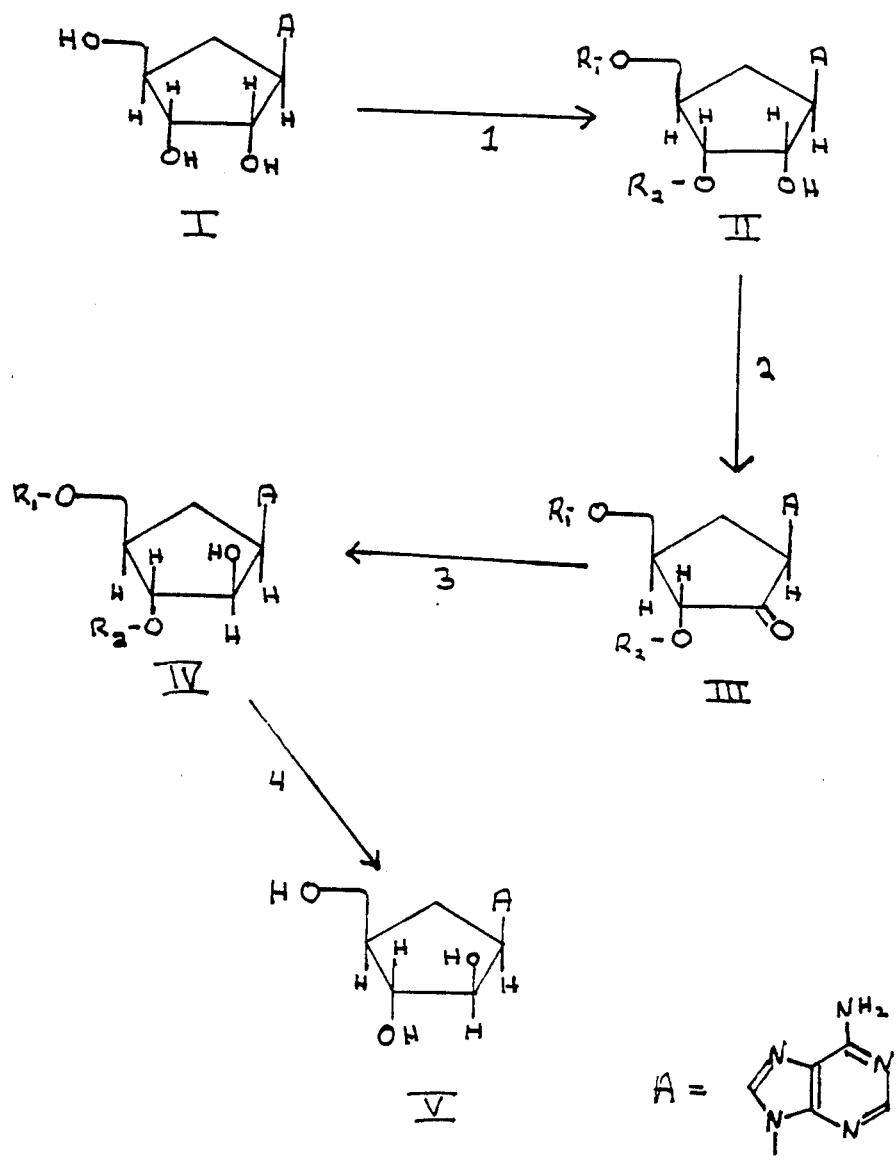

CONVERSION OF ARISTEROMYCIN INTO CYCLARADINE

BACKGROUND OF THE INVENTION

This invention relates to the conversion of aristeromycin into cyclaradine via stereoselective reduction of 3',5'-di-O-protected-2'-keto derivatives of aristeromycin.

Cyclaradine is a known compound which exhibits antiviral activity against the Herpes simplex virus types 1 and 2 and the Vaccina virus.

Vince et al. (U.S. Pat. No. 4,138,562) disclose a multistep, low yield synthesis of cyclaradine from 2-azabicyclo[2.2.1]hept-5-en-3-one.

T. L. Nagabhushan et al. (Abstracts of Papers presented at the 185th ACS National Meeting, Seattle, Wash., Mar. 20-25, 1983, CARB, paper #27) disclose a multistep synthesis of (+)-cyclaradine from (−)-aristeromycin via backside displacement of the 2'-O-triflate group by acetate ion. However, the synthesis is hampered by a low yield of cyclaradine and formation of side-products which are removed by use of expensive purification steps.

There is a need for a process for the conversion of aristeromycin into cyclaradine in high yield and substantially free of chemical and optical impurities without employing expensive purification procedures.

SUMMARY OF THE INVENTION

The present invention provides an improved process for conversion of aristeromycin into cyclaradine wherein a 3',5'-di-O-protected derivative of aristeromycin is converted into a 3,5'-di-O-protected cyclaradine which is thereafter deprotected to give cyclaradine, wherein the improvement comprises the steps of (a) reacting a 3',5'-di-O-protected derivative of aristeromycin with an effective amount of an oxidizing agent to produce a 3',5'-di-O-protected-2'-keto derivative of aristeromycin and then (b) reacting said 2'-keto derivative of aristeromycin with an effective amount of stereoselective reducing agent to produce a 3',5-di-O-protected derivative cyclaradine.

The present invention also provides compounds represented by formula III:

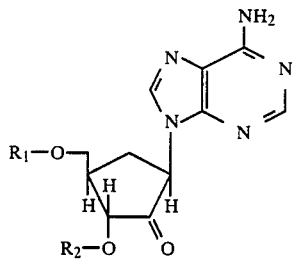

wherein $R_1$ and $R_2$ are readily removeable hydroxy-protecting groups which may be the same or different and may form part of a cyclic system.

The present invention further provides a process for conversion of aristeromycin into cyclaradine which comprises (a) reacting aristeromycin with an effective amount of a readily removable hydroxy-protecting group reagent to produce a 3',5'-di-O-protected derivative of aristeromycin; (b) reacting the product of step (a) with an effective amount of an oxidizing agent to produce the 3',5'-di-O-protected-2'-keto derivative of aristeromycin; (c) reacting the product of step (b) with an effective amount of a stereoselective reducing agent to produce a 3',5'-di-O-protected derivative of cyclaradine; and (d) removing the 3',5'-di-O-protecting groups from the product of step (c) to produce cyclaradine.

The present invention still further provides a process of converting (−)-aristeromycin into (+)-cyclaradine which comprises (a) reacting (−)-aristeromycin with an effective amount of readily removable hydroxy-protecting group reagent to produce a 3',5'-di-O-protected derivative of (−)aristeromycin; (b) reacting the product of step (a) with an effective amount of an oxidizing agent selected from dimethyl sulfoxide or chromium (VI) oxide to produce 3',5'-di-O-protected-2'-keto derivative of (−)-aristeromycin; (c) reacting the product of step (b) with an effective amount of a stereoselective boron-containing reducing agent to produce a 3',5'-di-O-protected derivative of (+) cyclaradine substantially free of (−)-cyclaradine; and (d) removing the 3',5'-di-O-protecting groups from the product of step (c) to produce substantically chemically and optically pure (+)-cyclaradine.

BRIEF DESCRIPTION OF THE FIGURE

The sole FIGURE is a Schematic of a preferred embodiment of the process of the present invention.

DETAILED DESCRIPTION OF THE INVENTION AND OF THE PREFERRED EMBODIMENTS

The present invention provides an improved process for the conversion of aristeromycin into cyclaradine by use of a sequence of reactions which minimizes the production of side-products and allows production of cyclaradine in higher yield than obtained with the prior art process disclosed in the Abstracts of Papers at the 185th ACS National Meeting. Compared to this prior art process, the present invention eliminates one step and reduces the need for multiple, expensive column chromatographic separations.

In its broadest aspect, the present invention provides selective oxidation of a 3',5'-di-O-protected derivative of aristeromycin with an effective amount of an oxidizing agent to produce the 3',5'-diprotected-2'-keto derivative of aristeromycin and a stereoselective reduction of said 2'-keto-derivative of aristeromycin with a stereoselective reducing agent to produce 3',5'-di-O-protected drivative of cyclaradine.

The term "readily removable hydroxy-protecting groups" as used herein means any such group conventionally used for this purpose with the only requirement being compatability with the hydroxy substituents on aristeromycin and cyclaradine derivatives and removeability utilizing conventional reagents used for this purpose which will not adversely affect the aristeromycin and cyclaradine structures.

Typical suitable readily removable hydroxy-protecting groups are disclosed in "Protective Groups in Organic Synthesis" by T. W. Greene, Wiley-Interscience, N.Y., Chapter 2 (Protection of the Hydroxyl Group Including 1,2- and 1,3-Diols), pp. 10-86. Exemplary readily removable hydroxy protecting groups include substituted methyl groups, especially arylalkoxymethyl of the formula $ArOCH_2$—, such as benzyloxymethyl; tertiaryalkoxymethyl such as tert-butoxymethyl; beta-substituted halo($C_2$–$C_6$) alkoxymethyl, such as 2,2,2-trichloroethoxymethyl; substituted ethyl groups especially 2,2,2-trichloroethyl; silyl groups such as tri(C$_1$-C$_6$)alkylsilyl such as trimethylsilyl, triethylsilyl, isopropyldimethylsilyl and tert-butyldimethylsilyl; beta-substituted-halo(C$_2$-C$_6$)alkanoyl such as chloroacetyl, trifluoroacetyl and dichloropropionyl; dialkanoyl groups of the formula (CH$_2$)$_n$(CO)$_2$ wherein n=2, 3, or 4, especially n=2; 1,3-(1,1,3,3-tetra(C$_1$-C$_6$)alkyldisiloxanyl groups of the formula O(SiR$_3$R$_4$)$_2$ wherein R$_3$ and R$_4$ are straight and branched-chain alkyl groups of 1-6 carbon atoms, such as methyl, ethyl or isopropyl; 1,3-(1,1,3,3-tetraisopropyldisiloxanyl is especially preferred; groups of the formulas

R$_5$R$_6$OC< and R$_5$OR$_6$OC< wherein R$_5$ and R$_6$ are independently straight and branched-chain alkyl groups of 1-6 carbon atoms such as methyl ethyl, isopropyl, C$_6$-C$_{10}$ aryl, especially phenyl, arylalkyl, especially benzyl or hydrogen. Exemplary

groups include

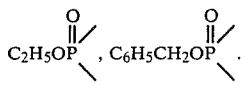

Exemplary R$_5$R$_6$OC< include H(CH$_3$O)C<, H(C$_2$H$_5$O)C<. Exemplary R$_5$OR$_6$OC< groups include (CH$_3$O)$_2$C<.

Typical suitable readily removable hydroxy protecting group reagents include halogen derivatives especially the chloro derivatives of the readily removable hydroxy protecting groups described hereinabove except those of the formulas R$_5$R$_6$OC< and R$_5$OR$_6$OC<. The preparation, use and removal of the readily removable hydroxy protecting groups are described in "Protective Groups in Organic Synthesis", Chapter 2 pp. 10-86. The preferred readily removable hydroxy protecting group reagent is 1,3-dichloro-1,1,3,3-tetraisopropyldisiloxane.

By use of the readily removable hydroxy-protecting groups of the present invention, the present invention affords regioselective oxidation of only the 2' hydroxy group.

The processes of the present invention are illustrated by the series of reactions number 1 to 4 in the following Scheme.

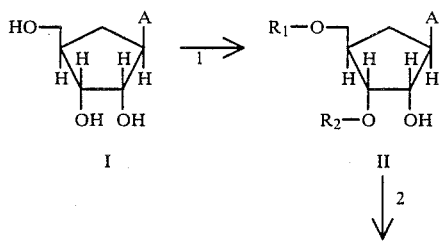

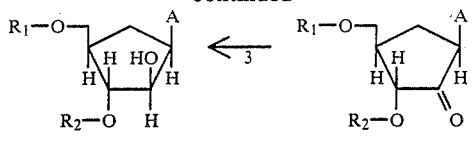

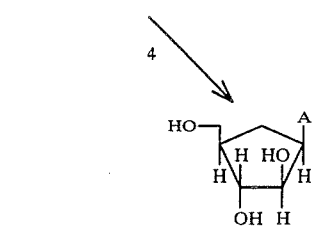

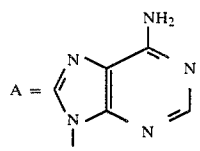

wherein R$_1$ and R$_2$ are as defined hereinabove.

Reaction (1) is normally carried out with aristeromycin (which may be isolated from *Streptomyces citricolor* as described by T. Kusaka et al. in The Journal of Antiobiotics Vol. XXI pp. 255-263 (1968) and at least about a stoichiometric amount of the readily removable hydroxy protecting group reagent at about 5° to about 50° C. in the presence of a base such as pyridine, 4-dimethylaminopyridine or triethylamine in an inert organic solvent such as dimethylformamide (DMF). While readily removable hydroxy protection group reagents such as 1,3-dichloro-1,1,3,3-tetraisopropyldisiloxyane or

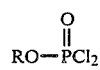

which form a cyclic system with the 3' and 5' oxygen are preferred, use of, for example, betahaloalkanoyl halides, e.g., chloroacetylchloride are also efficient. The reaction normally is complete in about two and one-half to four hours. The crude product may be purified by column chromatography, but preferably the organic solvent is removed and the sludge so formed is dissolved in ethyl acetate and solution is washed sequentially with water, 1% aqueous HCl, aqueous NaHCO$_3$ and brine. The resultant organic solution is dried and evaporated to a foam which is used directly in reaction (2).

In reaction (2), compound II is reacted with an effective amount of an oxidizing agent to produce the 3',5'-di-O-protected-2'-keto derivative of aristeromycin represented by formula III. The selective oxidizating reaction is carried out in an inert organic solvent, e.g., methylene chloride at a temperature of from −60° to 75° C. depending on the selective oxidizing agent chosen.

Typical suitable oxidizing agents and reactions temperatures include: oxalyl chloride and dimethyl sulfoxide (DMSO) at −60° C. to about −30° C.; DMSO and acetic anhydride or DMSO and trifluoroacetic anhydride at about 25° C. to about 75° C.; a complex of sulfur trioxide and pyridine and DMSO at about 5° to about 50° C. CrO₃/acetic acid/pyridine also may be used as the selective oxidizing agent, but yields of III are only about 50%.

An effective amount of the selective oxidizing agent is normally about 1-4 times the stoichiometric amount. The reaction is normally complete in about 2 hours. Base, typically tertiary $C_1$-$C_6$ alkylamines, e.g., but also triethylamine is then added and thereafter the reaction mixture is carefully treated with water. The organic layer is separated and washed with brine and concentrated to a residue which is used directly in reaction (3).

Preferred compounds represented by formula III

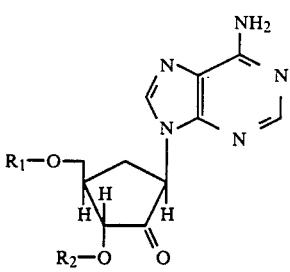
III include those wherein $R_1$ and $R_2$ taken together form a cyclic system with the 3',5' oxygen atoms, e.g. IIIa-

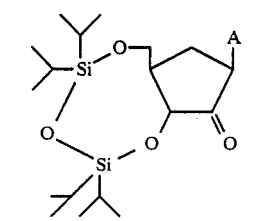
IIIa

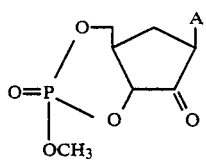
IIIb

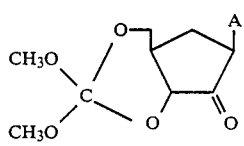
IIIc

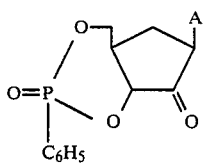
IIId

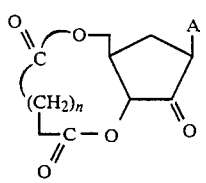
IIIe n = 2, 3 or 4

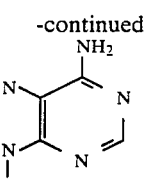
-continued

In reaction (3), the 2'-keto-derivative of aristeromycin (III) is reacted with an effective amount of a stereoselective reducing agent to produce the 3',5'-di-O-protected cyclaradine.

By the term "stereoselective reducing agent" as used herein means a reducing agent which reduces compounds of the formula III to produce 3',5'-di-O-protected cyclaradine substantially free, i.e., containing less than about 10 weight % of 3',5'-di-O-protected aristeromycin.

The typical suitable stereoselective boron-containing reducing agent include $R_7NH_2 \cdot BH_3$, $(R_7)_2BH$, $R_7BH_2$ or $M(R_7)_nBH_{4-n}$ wherein $R_7$ is a straight or branched chain alkyl group of 3 to 10 carbons, a carbocyclic a heterocyclic or heterocyclic group, n is 0, 1, 2 or 3 and M is an alkali metal.

The branched chain alkyl groups such as tert-butyl, neopentyl, isopentyl are preferred. Carbocyclic groups include $C_6$-$C_{16}$ carbocyclics, such as

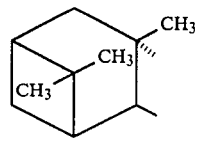

Heterocyclic groups include morpholine and 2,6-butidine.

A stereoselective boron containing reducing agent may be obtained by reaction of this cyclic trialkylborane such as cis, cis,trans-perhydro-9b-boraphenalene (H. C. Brown et al. J.A.C.S. 92, 709 (1970) with excess lithium hydride. Other useful regio- and stereoselective boron containing reducing agents are disclosed in "Modern Synthetic Reactions" 2nd Edition, H. O. Hovse W. A. Benjamine, Inc. N.Y. 1972 pp. 54-70.

Typical suitable stereoselective reducing agents also include sterically bulky boranes or borane amine complexes such as tert-butylamine borane complex, lithium tri(sec-butyl)borohydride, lithium thexyllimonylborohydride [J. Am. Chem. Soc. 93, 1491, 7319 (1971)], or even NaBH₄. The preferred stereoselective reducing agents such as tert-butylamineborane complex and lithium tri-(sec-butyl)borohydride provide almost 100% regio selectivity (addition of hydride from below to give only cyclaradine; NaBH₄ provides 10% aristeromycin, 90% cyclaradine and is less preferred. The reduction is carried out in a suitable inert organic solvent such as tetrahydrofuran (THF), ethyl acetate or methylene chloride at about 5°-25° C. An effective amount of the stereoselective reducing agent is normally about 1-5 times the stoichiometric amount. The reaction is normally complete in about 0.5 to 1 hour. Thereafter, the reaction mixture is diluted with water and the product extracted with, for example, ethyl acetate and the organic layer is washed with brine and evaporated to a residue, which is thereafter dissolved in methanol. The methanol solution is concentrated to induce crystallization. The crystals of the 3',5'-di-O-protected derivative of cyclaradine (Compound IV) are separated and the mother liquors may be chromatographed to obtain additional amounts of Compound IV and Compound II which may be recycled to reaction (2).

In reaction (4), the readily removeable hydroxy protecting groups are removed from Compound IV to produce cyclaradine, Compound V. In a preferred embodiment of the present invention wherein $R_1$ and $R_2$ are 1,3-(1,1,3,3-tetraisopropyldisiloxanyl), a solution of compound IV in an aprotic organic solvent, e.g., THF is treated with halide, e.g., fluoride ion at 5°–65° C. for about 1 to 12 hours to produce a solution of cyclaradine. The solution is extracted with water and the aqueous solution is cooled to allow crystallization of cyclaradine. Additional amounts of cyclaradine may be recovered from the aqueous mother liquors by standard techniques, such as extraction, chromatography and crystallization.

Typical suitable sources of fluoride ion include tetra-n-butylammonium fluoride and tetra-n-butylammonium bromide with at least a stoichiometric amount of potassium fluoride. Although the prior art (give reference) teaches that use of tetrabutylammonium bromide and potassium fluoride is not effective for readily removal hydroxy protecting groups, we have found tetra-n-butylammonium bromide and at least a stoichiometric amount of potassium fluoride completely removes the protecting groups when Compound IV is reacted with tetra-n-butylammonium bromide and at least a stoichiometric amount of potassium fluoride in refluxing THF/acetonitrile for 12 hours.

When other readily removable hydroxy protecting groups are used, removal may be effected using conditions disclosed in "Protective Groups in Organic Chemistry" by T. W. Greene, Chapter 2, pp. 10–86.

When the reactant is optically pure (−)-aristeromycin, (+)-cyclaradine is obtained substantially optically and chemically pure, i.e., containing less than about 10% of (−)-aristeromycin and in an amount about 3 times greater than obtained by the prior art process employing the triflate displacement procedure. The significantly higher yields of cyclaradine are obtained by the process of the present invention by eliminating one synthetic step and all the major column chromatography procedures.

EXAMPLE 1

(−)-3',5'-Tetra-isopropyldislox-1",3"-diylaristeromycin

Heat a stirred suspension of (−)aristeromycin (1.0 Kg; 75% pure; 2.87 mole) in 8.2 L of dry dimethylformamide (DMF) at 90° C. for 1 h. Cool the reaction mixture to ambient temperature and add 4-dimethylaminopyridine (DMAP) (500 g; 4.1 mole) and triethylamine (1.7 L; 1.23 Kg; 12.2 mole). Next add 1,3-dichloro-1,1,3,3,-tetraisopropyldisiloxane (1.2 Kg; 3.81 mole) over 0.5 hr and continue stirring for an additional 2 hrs. Add 500 mL of water and concentrate the reaction mixture to ~3 L of sludge. Slurry the solids in ~8 L of acetone and remove the insoluble 4-DMAP.HCl by filtration. Concentrate the filtrate to a oily residue.

Dissolve the oil in about 5 L of methylene chloride and chromatograph on 15 Kg of silica gel. Elute the column successively, with: 150 L of $CH_2Cl_2$, 300 L of 2% $MeOH/CH_2Cl_2$ (v/v) and 100 L of 5% $MeOH/CH_2Cl_2$ (v/v).

Combine the fractions containing the title compound and concentrate to give 173 Kg. (2.26 mole; 79% of theory of the title compound as a foam).

It was found that purification of the title compound via column chromatography was not necessary. Alternatively, after concentration of the reaction mixture to remove the DMF, dissolve the sludge in ethyl acetate and wash the solution sequentially with $H_2O$, 1% aqueous HCl, water, aqueous $NaHCO_3$ and brine. Concentrate the organic layer to give the title compound as a foam which may be used directly in the next step.

EXAMPLE 2

3'-5'-Tetra isopropyldisolox-1",3"-diyl-2-Keto Derivative of Aristeromycin

To a cold (−72° C.), stirred solution of oxalyl chloride (100 ml; 145.5 g; 1.15 mole) in 2.5 L of methylene chloride, add a solution of dimethyl sulfoxide (170 ml; 187.2 g; 2.4 mole) in 0.5 L of methylene chloride over 15 minutes. Stir for an additional 1 hr. at −72° C. Add a solution of title compound of Example 1 (500 g; 0.99 mole) in 1 L of methylene chloride, maintaining the temperature below −65° C. Stir for 15 minutes at −72° C., then add triethylamine (700 ml; 508 g; 5.03 mole) maintaining the temperature below −65° C. (Addition time ~15 minutes). Stir at −72° C. for 15 minutes, then warm the reaction to ambient temperature over 1.5 hr. Extract the reaction mixture with water and brine and concentrate the organic layer to give 552.3 g of the title compound as a residue.

EXAMPLE 3

(+)-3',5'-Tetra isopropyldisolox-1",3"-diylcyclaradine

Dissolve the residue from Example 2 in 2.7 L of dry THF and slowly add tert-butylamine borane (100 g; 1.5 mole). Stir the reaction for 0.5 h. Add 1 L of water and extract the product with ethyl acetate. Wash the organic layer with brine and concentrate to a residue. Add methanol (~1 L) and concentrate to induce crystallization. Store at 5° C. overnight. Collect the product by filtration, wash with cold methanol and dry under vacuum at 50° C. to give 266 g (0.525 mole; 53% yield) of the title compound. An additional 100 g (0.197 mole; 20% yield) of the title compound is obtained by column chromatography of the mother liquors.

EXAMPLE 4

(+)-Cyclaradine)

Add 950 mL of a 1M solution of tetra-n-butylammonium fluoride in THF to a stirred solution of the title compound of Example 3 (459 g; 0.91 mole) in 2 L of THF. Stir the reaction mixture at ambient temperature for 1 h. Concentrate the mixture to ~0.5 L and add ethyl acetate (2 L) and water (2 L). Concentrate the aqueous layer to ~1.5 L and seed with an authentic sample of crystalline cyclaradine. Refrigerate overnight, then collect the solids by filtration, wash with cold water and acetone, and dry under vacuum at 50° C. to give 177.5 g (0.670 mole; 74%) of the title compounds, $[\alpha]_D^{26}+61.3$ (C, 2%, DMF). Concentrate the mother liquors to remove the acetone, then pass the aqueous solution through a column of 1 L of activated granular carbon (Darco). Wash the column with water and elute the cyclaradine with acetone:water (1:1). Combine the appropriate fractions and concentrate to ~500 mL. Dry under vacuum at 50° C. to give 34.9 g (0.132 mole, 14.5%) of the title compound, $[\alpha]_D^{26} + 60.2$ (C, 2%, DMF).

What is claimed is:

1. An improved process for conversion of aristeromycin into cyclaradine wherein 3′,5′-di-O-protected derivative of aristeromycin is converted into 3′,5′-di-O-protected derivative of cyclaradine which is thereafter deprotected to give cyclaradine, wherein the improvement comprises the steps of (a) reacting a 3′,5′-di-O-protected derivative of aristeromycin with an effective amount of an oxidizing agent to produce a 3′,5′-di-O-protected-2′-keto derivative of aristeromycin and then (b) reacting said 2′-keto derivative of aristeromycin with an effective amount of stereoselective reducing agent to produce 3′,5′-di-O-protected derivative of cyclaradine.

2. A process of claim 1 wherein (−) aristeromycin is converted into substantially optically and chemically pure (+) cyclaradine.

3. A process for conversion of aristeromycin into cyclaradine which comprises (a) reacting aristeromycin with an effective amount of a readily removable hydroxy-protecting group reagent to produce a 3′,5′-di-O-protected derivative of aristeromycin; (b) reacting the product of step (a) with an effective amount of an oxidizing agent to produce the 3′,5′-di-O-protected-2′-keto derivative of aristeromycin; (c) reacting the product of step (b) with an effective amount of a stereoselective reducing agent to produce a 3′,5′-di-O-protected derivative of cyclaradine; and (d) removing the 3′,5′-di-O-protecting groups from the product of step (c) to produce cyclaradine.

4. A process of claim 3 wherein the reactant is (−)-aristeromycin and the product is (+)-cyclaradine.

5. A process of claim 3 wherein in step (a) a removable hydroxy protecting group reagent capable of forming a cyclic system with the 3′ and 5′ oxygens of aristeromycin is used.

6. A process of claim 3 wherein step (b) dimethyl sulfoxide is the oxidizing agent.

7. A process of claim 3 wherein the step (c) a bulky alkyl borane or an alkali metal bulkalkyl borohydride is the stereoselective reducing agent.

8. A process of converting (−)-aristeromycin into (+)-cyclaradine which comprises (a) reacting (−)-aristeromycin with an effective amount of a readily removable hydroxy-protecting group reagent to produce a 3′,5′-di-O-protected derivative of (−)aristeromycin; (b) reacting the product of step (a) with an effective amount of an oxidizing agent selected from dimethyl sulfoxide or chromium (VI) oxide to produce a 3′,5′-di-O-protected-2′-keto derivative of (−)-aristeromycin; (c) reacting the product of step (b) with an effective amount of a stereoselective boron-containing reducing agent to produce the 3′,5′-di-O-protected derivative of (+)-cyclaradine substantially free of (−)-cyclaradine; and (d) removing the 3′,5′-di-O-protecting groups from the product of step (c) to produce substantially chemically and optically pure (+)-cyclaradine.

9. A process of claim 7 wherein in step (a) the readily removeable hydroxy-protecting group reagent is 1,3-dihalo-1,1,3,3-tetraloweralkyldisiloxane.

10. A process of claim 7 wherein in step (d) fluoride ion in an aprotic solvent is used to remove the 3′,5′-bis-1,3-(1,1,3,-3-tetra($C_1$–$C_6$)alkyldisiloxanyl) protecting group.

11. A process of claim 7 wherein the stereoselective boron-containing reducing agent is selected from $R_7NH_2.BH_3$, $(R_7)_2BH$, $R_7BH_2$ or $M(R_7)_nBH_{4-n}$ wherein $R_7$ is a straight or branched chain alkyl group of 3 to 10 carbons, a carbocyclic group, a heterocyclic group or heteroaromatic group, n is 0, 1, 2, or 3 and M is an alkali metal.

12. A process of claim 11 wherein said boron-containing reducing agent is $(CH_3)_3CNH_2.BH_3$.

13. A process of claim 10 wherein said boron-containing reducing agent is $[(CH_3)_2CHCH(CH_3)_2]_2BH$.

* * * * *